United States Patent [19]

Zare et al.

[11] Patent Number: 5,092,973
[45] Date of Patent: Mar. 3, 1992

[54] RECTANGULAR CAPILLARIES FOR CAPILLARY ELECTROPHORESIS

[75] Inventors: Richard N. Zare, Stanford; Jonathan V. S. Sweedler, Redwood City; Takao Tsuda, Palo Alto, all of Calif.

[73] Assignee: The Board of Trustees of the Leland Stanford Junior University, Stanford, Calif.

[21] Appl. No.: 470,390

[22] Filed: Jan. 26, 1990

[51] Int. Cl.[5] .................. G01N 27/26; B01D 57/02
[52] U.S. Cl. .......................... 204/182.1; 204/180.1; 204/299 R
[58] Field of Search ............ 204/299 R, 182.1, 180.1; 428/34.1, 34.6, 34.4, 34.7, 35.1, 35.7, 36.9, 36.91, 36.92

[56] References Cited

U.S. PATENT DOCUMENTS

| | | | |
|---|---|---|---|
| 3,822,411 | 7/1974 | Merle | 333/241 |
| 3,939,439 | 2/1976 | Fletcher et al. | 350/96.12 X |
| 3,974,467 | 8/1976 | Tobita et al. | 333/241 |
| 4,584,474 | 4/1986 | Faunchy et al. | 250/505.1 X |
| 4,660,932 | 4/1987 | Eckbreth | 350/171 |
| 4,690,749 | 9/1987 | Van Alstine et al. | 204/299 R |

OTHER PUBLICATIONS

Gebauer et al., "Determination of Nitrate, Chloride and Sulphate in Drinking Water by Capillary Free-Zone Electrophoresis", J. Chromatogr., vol. 267, 1983, pp. 455-457.

Caldwell, "Field-Flow Fractionation", Anal. Chem., vol. 60, No. 17, Sep. 1, 1988, pp. 959A-971A.

Gordon et al., "Capillary Electrophoresis", Science, vol. 242, 1988, pp. 224-228.

Huang et al., "Quantitative Analysis of Low Molecular Weight Carboxylic Acids by Capillary Zone Electrophoresis/Conductivity Detection", Anal. Chem., vol. 61, No. 7, 1989, pp. 766-770.

Thormann, W. et al., "Focusing Counterparts of Electrical Field Flow Fractionation and Capillary Zone Electrophoresis-Electrical Hyperlayer Field Flow Fractionation and Capillary Isoelectric Focusing", Journal of Chromatography, 461 (1989) 95-101.

Jan a, J. and Nováková N. "Retention in Sedimentation-Flotation Focusing Field-Flow Fractionation Using a Step Density Gradient", Journal of Chromatography, 452(1988) 549-562.

Werner G. Kuhr "Capillary Electrophoresis", Analytical Chemistry 62, 403R-414R.

Primary Examiner—John Niebling
Assistant Examiner—John S. Starsiak, Jr.
Attorney, Agent, or Firm—Majestic, Parsons, Siebert & Hsue

[57] ABSTRACT

An elongated or rectangular cross-section capillary is disclosed for use in capillary electrophoresis using optical detection. With rectangular capillaries, heat is efficiently dissipated which permits large volume applications in capillary electrophoresis. In addition, the increase in cell pathlength produces significant improvements in absorbance detection sensitivity. This advantage is also important for laser-induced fluorescence, optical rotation, and other pathlength-dependent detection schemes. Because flat walls produce less optical distortion than circular capillary walls, rectangular capillaries are particularly useful when parameters such as refractive index, photodeflection, direct visualization or particle counting are used for detection. Capillary electrophoresis employing rectangular capillaries allows for two-dimensional separations.

13 Claims, 6 Drawing Sheets

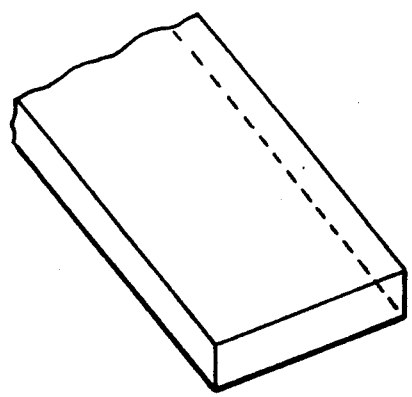
FIG._1.
FIG._2.
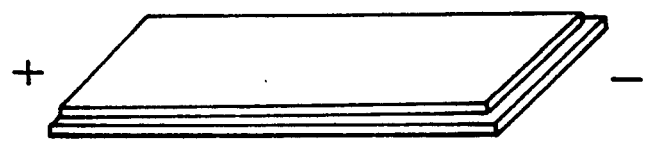
FIG._3.
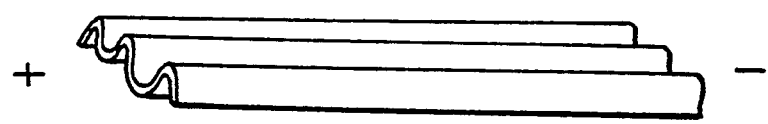
FIG._4.

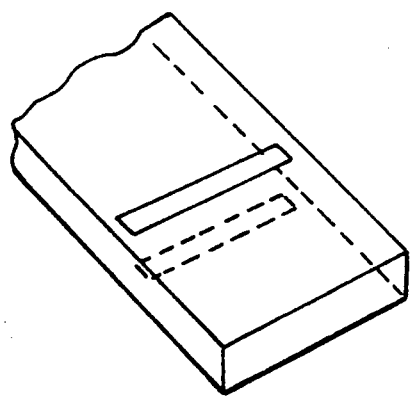
FIG._5.
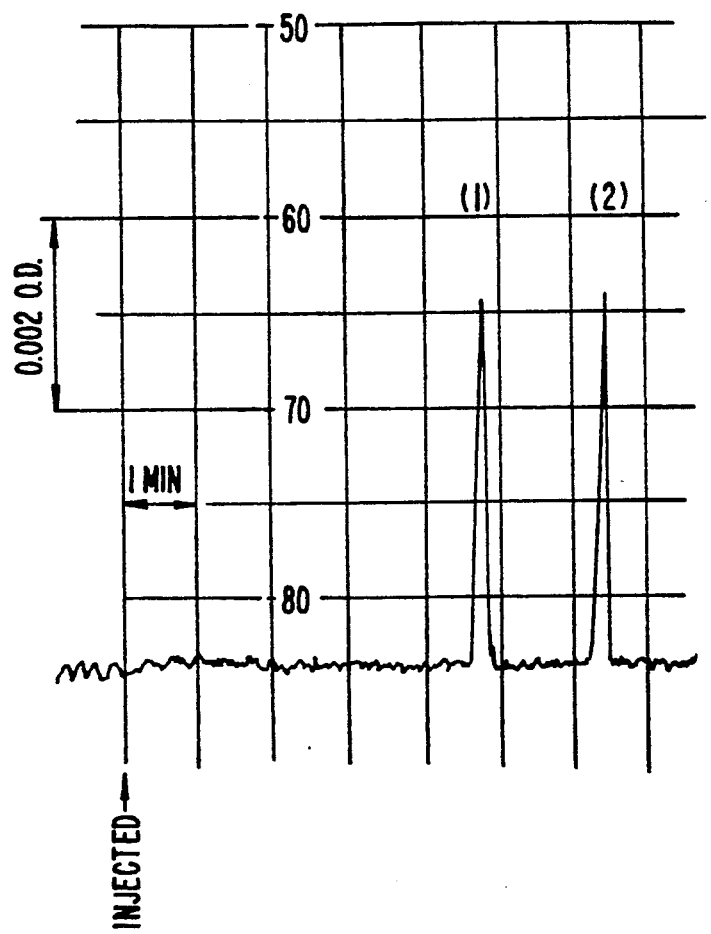
FIG._6.

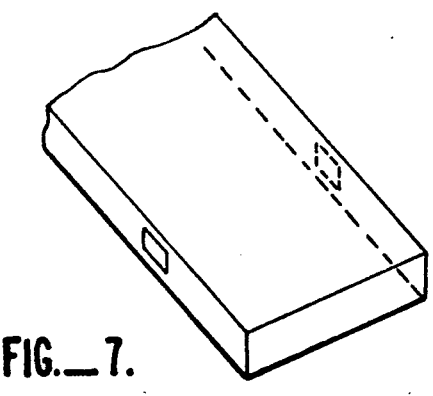
FIG._7.
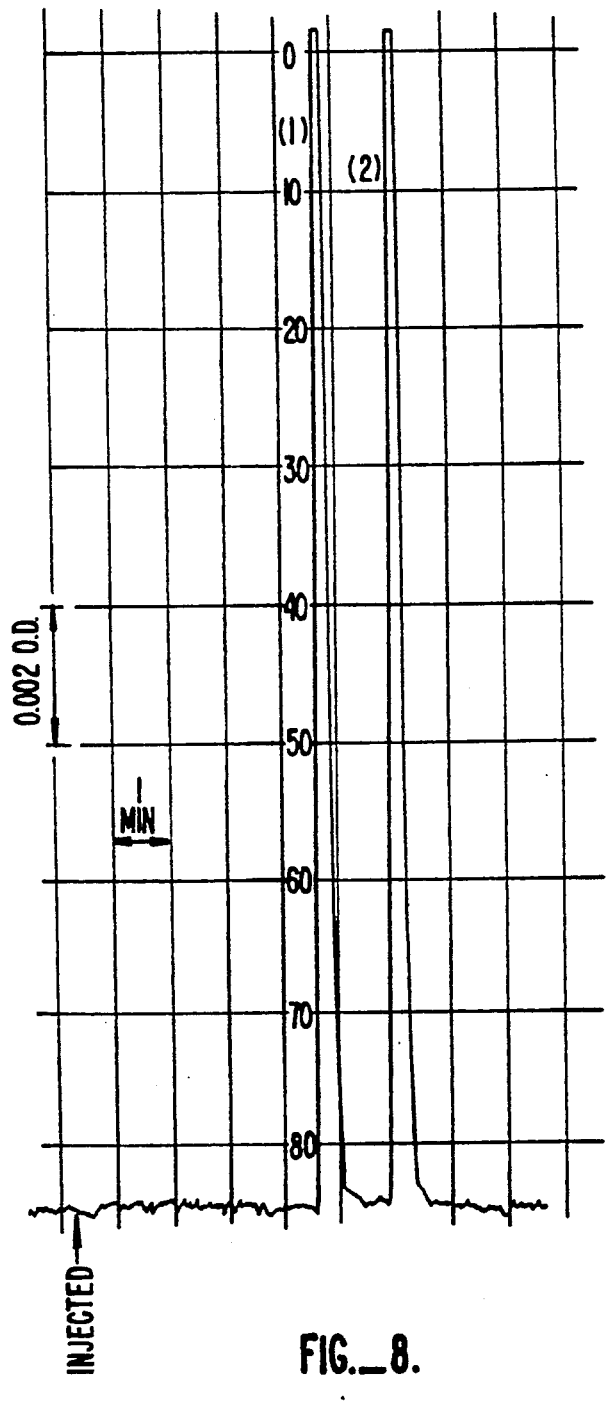
FIG._8.

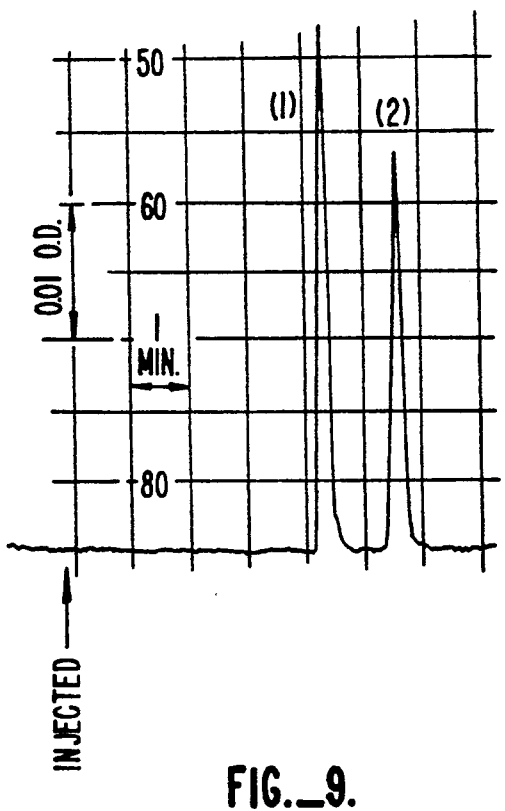
FIG._9.
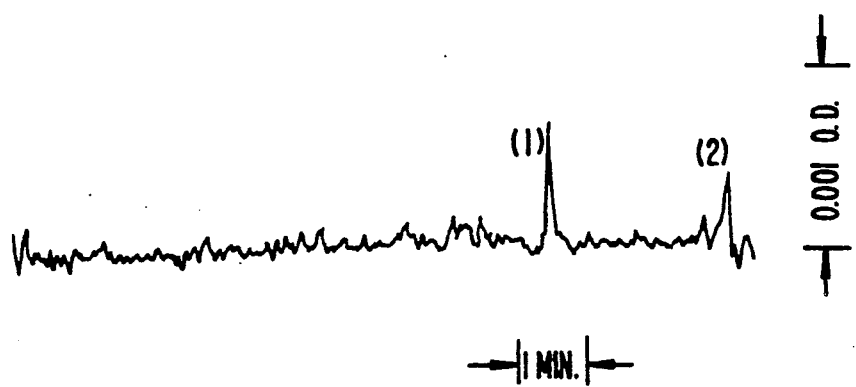
FIG._10.

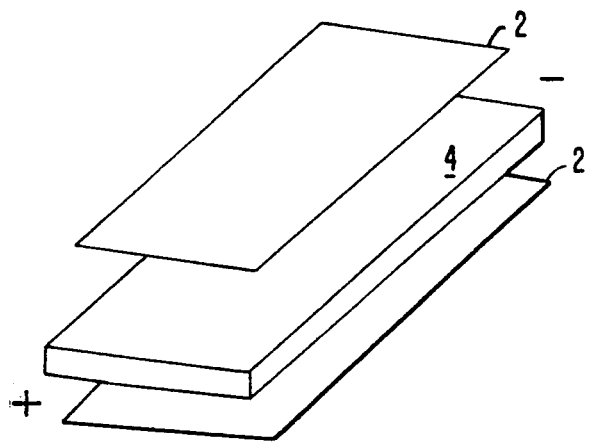
FIG._11.
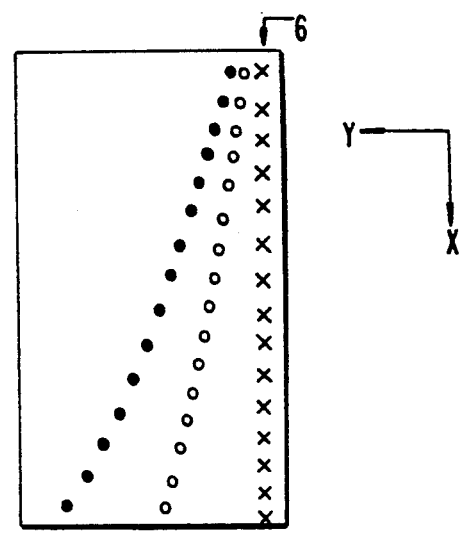
FIG._12.
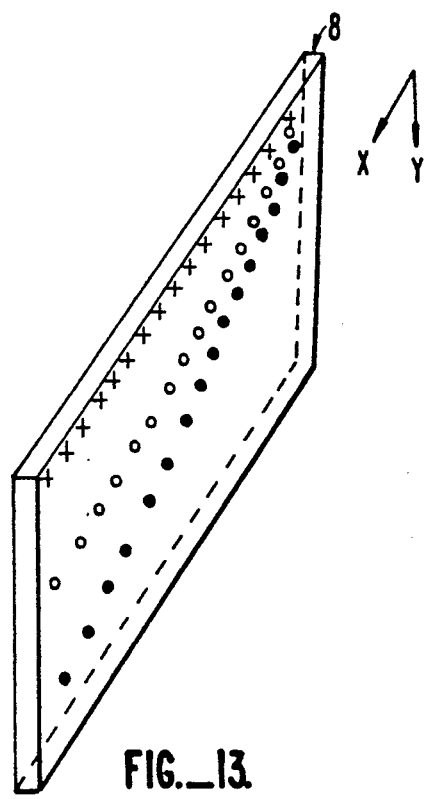
FIG._13.

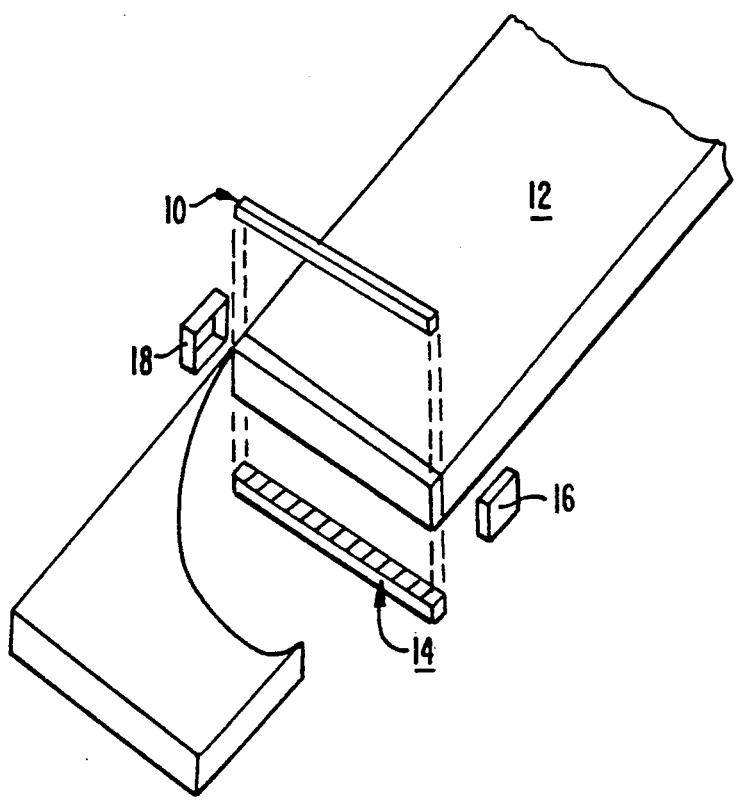
FIG._14.

RECTANGULAR CAPILLARIES FOR CAPILLARY ELECTROPHORESIS

BACKGROUND OF THE INVENTION

This invention relates in general to capillary devices and in particular to rectangular capillaries useful in capillary electrophoresis (CE), particularly in capillary zone electrophoresis (CZE).

Capillary electrophoresis is one of the most powerful separation techniques for the analysis of a wide variety of complex mixtures. The technique is capable of orders of magnitude higher resolution than high-performance liquid chromatography; moreover, with CE work it is possible to analyze nanoliter samples. In the past, separation in CE has been exclusively performed in circular capillaries with internal diameters between 5 and 200 microns. The small size of the capillary allows extremely efficient heat dissipation, but as the capillary dimensions are increased beyond 100 microns, a dramatic decrease in separation efficiency is observed. Consequently, CE cannot be scaled to larger diameter capillaries, even with efficient cooling of the outside of the capillary by heat transfer fluids. Furthermore, with circular capillaries, CE cannot be used for ultra-low concentration applications. That is, while the mass sensitivity of CE is outstanding, detection methods still remain the "Achilles heel" of the technique. The ability to detect low concentrations in a 100 micron capillary is difficult, especially when using the very common technique of UV-Vis absorbance.

Another inherent problem associated with conventional circular capillaries is the optical distortion caused by the curvature of the capillary walls. This problem is particularly important when optical detection means are utilized. For example, the curvature at the solute (liquid)-wall interface or at the wall-atmosphere (detector) interface will adversely affect refractive index or photodeflection measurements. In addition, when direct counting methods are employed, the curvature of the capillary walls can cause inaccurate counts.

CZE in small capillaries has proven useful as an efficient method for the separation of solutes. An electric field is applied between the two ends of a capillary tube into which an electrolyte containing the solutes is introduced. The electric field causes the electrolyte to flow through the tube. Some solutes will have higher electrokinetic mobilities than other solutes so that the solutes form zones in the capillary tubes during the flow of the electrolytes through the capillary. However, Joule heating owing to the ionic current carried between the electrodes can result in temperature gradients and subsequent convection and density gradients that increase zone broadening, affect electrophoretic mobilities and even lead to boiling of solvent.

There is a critical need for a capillary device that handles large throughputs and dissipates heat efficiently in CE. Moreover, there is a need for capillary devices with sufficient cell pathlengths so that detection of low concentration samples are facilitated. Furthermore, the capillary device should create minimal optical distortions. Finally, conventional circular capillaries are not suitable for two-dimensional CE separation. A need exists for capllary devices that offer this option.

SUMMARY OF THE INVENTION

The device of this invention is for use in capillary electrophoresis. The device comprises a capillary with an elongated cross-section that is transparent at the detection point. In the preferred embodiment, the capillary has rectangular cross-sectional inner dimensions of approximately 50 by 1000 microns. The inventive devices are referred to below as rectangular capillaries. Various configurations of rectangular capillaries may be employed. These include flexible capillaries, ultra-thin channels formed between plates, and corrugated structures. With rectangular capillaries, ineffective heat dissipation no longer presents an obstacle to large volume CE applications. In addition, when optical detection techniques are used, the increase in cell optical pathlength produces significant improvements in detection sensitivity. This advantage is important for laser-induced fluorescence, optical rotation, and also other pathlength-dependent detection schemes. The flat walls produce less optical distortion compared to the walls of circular capillaries. This is particularly important when on column detection is based on parameters such as refractive index measurements, photodeflection, direct visualization or particle counting.

Capillary electrophoresis using rectangular capillaries allows for two-dimensional separations. For instance, creating any gradient across the separation channel of a rectangular capillary while applying an electric field along the length of the capillary provides for a two-dimensional separation.

BRIEF DESCRIPTION OF THE DRAWINGS

FIG. 1 shows a rectangular capillary.

FIG. 2 shows a rectangular capillary with a flexible configuration;

FIG. 3 shows flat, rigid, ultra-thin channels formed between two plates;

FIG. 4 shows a corrugated configuration formed by folding a rectangular capillary;

FIG. 5 shows a rectangular capillary with a slit situated on the top side of the capillary at which radiation from a detection device is directed;

FIG. 6 is an electropherogram obtained with absorbance detection using a rectangular capillary as shown in FIG. 5;

FIG. 7 shows a rectangular capillary with a slit situated on the side of the capillary at which radiation from a detection device is directed;

FIG. 8 is an electropherogram obtained with absorbance detection using a rectangular capillary as shown in FIG. 7;

FIG. 9 is an electropherogram obtained with absorbance detection using a rectangular capillary as shown in FIG. 7; and, FIG. 10 is an electropherogram obtained with absorbance detection using a rectangular capillary as shown in FIG. 7.

FIG. 11 is a perspective view of a rectangular capillary with magnets positioned to form a magnetic field across the separation channel.

FIG. 12 is the separation pattern for three solutes in two-dimensional separation using electric and magnetic field gradients.

FIG. 13 is the separation pattern for three solutes in two-dimensional separation using electric and gravitational field gradients.

FIG. 14 is a perspective view of a rectangular capillary and a detection device for two-dimensional separations.

DETAILED DESCRIPTION OF THE PREFERRED EMBODIMENTS

An elongated or rectangular cross-sectional capillary is more efficient than a circular capillary at heat dissipation because of greater surface-to-volume ratio; thus, larger (in volume) capillaries can be used while achieving separations with comparable resolution. The rectangular geometry allows the sample size to be increased by at least an order of magnitude—a very important increase when considering CE for preparative applications. The inner dimensions of the inventive rectangular capillaries are about 10 to 200 microns by about 200 to 4,000 microns or more. The inventive capillaries can be manufactured from materials currently used in circular capillaries, including fused silica or borosilicate glass. A rectangular capillary is shown in FIG. 1. A high voltage (+ —) is applied between the ends of the capillary to move solutes through it.

Besides the use of rectangular capillaries of different dimensions, this invention also encompasses rectangular capillaries of different configurations. For instance, FIG. 2 describes a flexible rectangular capillary that, for instance, can be readily inserted into two buffer reservoirs. FIG. 3 describes a rectangular capillary that consists of ultra-thin, rigid channels formed between two plates. The plates can be made of fused silica, ceramics, glass or Teflon ®. One method for producing ultra-thin channels is fused silica etching; another method is by using thin Teflon ® spacers. The distance between the plates are approximately 10 to 200 microns. Finally, FIG. 4 describes a corrugated structure formed by folding a rectangular capillary which provides larger cross-sectional areas. As is apparent, this corrugated arrangement does not truly have an elongated cross-section. Although this folded arrangement does not have the same optical pathlength advantage as demonstrated in the flexible rectangular capillary or the flat, rigid, ultra-thin channels, the corrugated arrangement is useful for preparative work.

The degree of detection sensitivity enhancement in CE with rectangular capillaries is ideally proportional to the increase in the pathlength when absorption, fluorescence, or circular dichroism is used. For instance, the use of a $50 \times 1000$ micron rectangular capillary provides a 1000 micron pathlength and results in a greater than ten-fold increase in sensitivity compared to an 50 micron pathlength capillary. This enhanced sensitivity is demonstrated by the following examples.

EXAMPLE I

A rectangular $50 \times 1000$ micron (inner dimensions) capillary made of borosilicate glass (Wilmad Glass Co., Buena, N.J.) was used in a prototype CZE apparatus. See Gordon et al., *Science*, 244 (1988) for a description of the CZE apparatus and Huang et al. *Anal. Chem*, 61:7, 766 (1989) for a description of the absorption detector used.

The sample consisted of pyridoxime (1) $2.5 \times 10^{-3}$M, and (2) dansylated-L-serine $2.9 \times 10^{-3}$M. The CZE separation was done under the following conditions:
Cell:pathlength 50 μm. Slit $50 \times 800$ μm. Split flow 0.5 ml/min. Split ratio 114. Injector's loop 5 μl. Recorder 1 cm/min. Full scale 0.02 O.D. Applied voltage 7.92 kV, current 107 μA. Column $50 \times 1000$ μm rectangular. Column length 50 cm. FIG. 5 shows that for Example I, the radiation from the detection device traverses the height of the rectangular cross-section of the capillary through the transparent slits or sections, thereby providing a 50 μm cell pathlength.

FIG. 6 is an electropherogram obtained with the detection geometry described in Example I.

EXAMPLE II

Using the same CZE apparatus and test sample as described in Example I, a CZE separation was performed under the following conditions:
Cell:pathlength 1000 μm. Slit $50 \times 100$ μm. Split flow 0.5 ml/min. Split ratio 114. Injector's loop 5 μl. Recorder 1 cm/min. Full scale: 0.02 O.D. Applied voltage: 9.48 kV, current 111 μA. Column $50 \times 1000$ μm rectangular. Column length 64 cm.

FIG. 7 shows that for Example II, the radiation from the detection device traverses the width of the rectangular cross-section of the capillary through the transparent slits on the sides of the capillary, thereby providing a 1000 μm cell pathlength.

FIG. 8 is an electropherogram obtained with the detection geometry described in Example II.

EXAMPLE III

Using the same CZE apparatus and test sample as described in Example II, a CZE separation was performed under the same conditions as in Example II, except as follows:
Recorder: full scale 0.1 O.D. Current: 113 μa.

FIG. 9 is an electropherogram obtained with the detection geometry described in Example III.

comparison of the electropherograms for Examples I and II (FIGS. 6 and 8, respectively) which were obtained at the same detector sensitivity illustrates the significant gain in sensitivity resulting from the greater pathlength in Example II. The increase in sensitivity due to an increase in pathlength is also illustrated i comparing the electropherograms for Example I with that of Example III (FIG. 9), the latter was obtained at a lower detector sensitivity. The gain attributed to the increase in cell pathlength can be readily calculated from the electropherograms.

Improvement in detection sensitivity caused by cell pathlength increase is most pronounced when the concentration of the sample is low. For instance, when the concentration of a sample is just sufficient to be detectable in a 50 μm cell pathlength rectangular capillary, by employing a rectangular capillary with a pathlength to 1000 μm, a gain of nearly 20 times is observed.

EXAMPLE IV

Using the same CZE apparatus and $50 \times 1000$ micron capillary as described in Example II, a CZE separation was performed with the following sample and under the following conditions:
Sample: pyridoxime (1) $1 \times 10^{-7}$M, and dansylated-L-serine (2) $1 \times 10^{-7}$M
Buffer: 5 mM phosphate buffer including 5% ethylene glycol
Cell:pathlength 1000 μm. Slit $50 \times 100$ μm.
Applied voltage 7.68 kV, current 75 μA.
Detection: 310 nm, 0.01 O.D. full scale.

The concentration of this sample is within the ultra-low range where capillary electrophoresis using conventional circular capillaries yields poor results. However, with the larger pathlength of rectangular capillaries, detection even at these low concentrations is practical. FIG. 10 is an electropherogram obtained with the detection geometry described in Example IV.

Besides improving UV-Vis absorbance techniques in CE, the pathlength advantage associated with rectangular capillaries is also important for laserinduced fluorescence, optical rotation, and other pathlength-dependent detection schemes. The rectangular capillary walls being flat instead of curved provide far less optical distortion than circular capillaries. This is important where parameters such as refractive index or photodeflection are used for detection.

Finally, CE using rectangular capillaries allows for two-dimensional separations. For instance, in FIG. 11, magnets 2 are positioned to create a magnetic field across the separation channel of a rectangular capillary 4. If an electric field is applied along the length of the capillary, two-dimensional separation occurs.

FIG. 12 illustrates a hypothetical two-dimensional separation of a sample containing three solutes A (●), B (○), and C (X) over a period of time. The x-axis designates movement of the solutes due to the electric field along the capillary and the y-axis designates movement of the solutes due to the magnetic field across the capillary. The sample is introduced into the capillary at position 6. As depicted, solute A is strongly affected by the magnetic field, while B is only moderately affected, and C is not affected.

FIG. 13 illustrates a hypothetical two-dimensional separation pattern of solutes D (●), E(○), and F (X) in a rectangular capillary where an electric field is applied along the x-axis and gravity acts as the force along the y-axis. The sample is introduced into the capillary at position 8. In this example, solute D, e.g., a large particle with high density, is strongly affected by gravity, E is moderately affected, and F is apparently unaffected by gravity.

Two-dimensional separation can also be accomplished by using pH, temperature and other gradients that will affect the solutes. In two dimensional separation, conventional detection devices such as absorption detectors, fluorescence detectors, Raman spectroscopy detectors, electrochemical detectors, and mass spectrometric detectors can be used. FIG. 14 is a perspective view of a detection apparatus for two-dimensional separations. As shown, light source 10 extends the width of one side of the rectanglar analytical capillary column 12. On the opposite side of column 12 is a multichannel detector array 14 to measure the positions and intensities of the solutes which pass by along the width of the capillary. The multichannel detector array thus measures how solutes are influenced by a gradient, e.g., magnetic field, formed across the rectangular capillary. As an option, a second light source 16 can be positioned along the side of the capillary column to focus light across the column. On the opposite side of the column is detector 18. Detector 18 functions to measure the total solute concentration, with the associated pathlength advantages.

It is to be understood that while the invention has been described above in conjunction with preferred specific embodiments, the description and examples are intended to illustrate and not limit the scope of the invention, which is defined by the scope of the appended claims.

It is claimed:

1. A method of detecting constituents in capillary electrophoresis, comprising the steps of:
    providing a capillary tube that has one or more transparent sections and having an elongated cross-section;
    introducing into the capillary tube a fluid containing a plurality of constituents that will move at different speeds when an electric field is applied along the length of the capillary tube;
    applying a separation gradient across the elongated cross-section causing the components of the sample to further separate in a direction transverse to the length of tube;
    positioning an optical detection device near the one or more transparent sections to measure light signals corresponding to said constituents, said signals having traversed the elongated cross-section; and
    applying an electric field along the length of the capillary tube.

2. The detection method as defined in claim 1 further comprising the step of:
    passing light through said one or more transparent sections;
    where the positioning step positions an array of detectors for detecting light signals that pass through said tube along locations in said transverse direction.

3. A capillary electrophoresis device for analyzing a sample, said sample including components that move at different speeds in an electric field, said device comprising:
    a capillary tube that has one or more transparent sections, said sections each having an elongated cross-section that is substantially rectangular in geometry wherein the shorter dimension of the cross-section defines the height of the cross-section and the longer dimension of the cross-section defines the width of the cross-section;
    means for applying an electric field along the length of the capillary so that when a sample is introduced into the capillary tube, the sample will separate into its components in the capillary tube; and
    optical means for detecting said components, said optical detection means positioned adjacent to the one or more transparent sections of the capillary tube to detect light signals that traverse the rectangular cross-section width.

4. The capillary electrophoretic device as defined in claim 3 further comprising means for providing light through the longer dimension of the one or more cross-sections.

5. The capillary electrophoresis device as defined in claim 4 wherein the inner dimensions of the rectangular cross-section are approximately 10 to 200 microns by at least about 200 microns.

6. The capillary electrophoresis device as defined in claim 5 wherein the inner dimensions of the rectangular cross-section are approximately 50 microns by 1000 microns.

7. A capillary electrophoresis device for analyzing a sample, said sample including components that move at different speeds in an electric field, said device comprising:
    a capillary tube that has one or more transparent sections, said sections each having an elongated cross-section that is substantially rectangular in geometry wherein the shorter dimension of the cross-section defines the height of the cross-section and the longer dimension of the cross-section defines the width of the cross-section;
    means for applying an electric field along the length of the capillary so that when a sample is introduced into the capillary tube, the sample will separate into its components in the capillary tube;

means for applying a separation gradient across the rectangular cross-section causing the components of the sample to further separate in a direction transverse to the length of the capillary tube; and optical means for detecting said components, said optical detection means positioned adjacent to the one or more transparent sections of the capillary tube to detect light signals that transverse the rectangular cross-section width.

8. The capillary electrophoresis device as defined in claim 7 wherein said means for applying a separation gradient create a temperature differential, a pH differential, an electric field, a magnetic field, or a gravitational field.

9. The capillary electrophoresis device as defined in claim 8 further comprising a detection apparatus to measure the separation of said components by said gradient.

10. The capillary electrophoresis device as defined in claim 9 wherein the optical detection means comprises a multichannel detector array positioned on one side of a transparent section and a light source on the other side.

11. A capillary electrophoresis device for analyzing a sample, said sample including components that move at different speeds in an electric field, said device comprising:

two plates that form a flat, rigid, ultra-thin elongated channel, said plates having one or more transparent sections, wherein the channel has an elongated cross-section that is substantially rectangular in geometry, the shorter dimension of the cross-section defining the height of the cross-section and the longer dimension of the cross-section defining the width of the cross-section and wherein the plates confine said sample;

means for applying an electric field along the length of the channel so that when a sample is introduced into the channel, the sample will separate into its components in the channel; and optical means for detecting said components, said optical detection means positioned adjacent to the one or more transparent sections to detect light signals that traverse the rectangular cross-section width.

12. The capillary electrophoresis device as defined in claim 11 further comprising means for providing light through the longer dimension of the one or more transparent cross-sections.

13. The capillary electrophoresis device as defined in claim 12 wherein the separation between the plates is in a range of approximately 10 to 200 microns.

* * * * *